United States Patent
Hamamoto et al.

(10) Patent No.: US 10,016,502 B2
(45) Date of Patent: Jul. 10, 2018

(54) PATCH PREPARATION CONTAINING AN ACID SCAVENGER

(71) Applicant: MEDRx CO., LTD, Higashikagawa-shi, Kagawa (JP)

(72) Inventors: Hidetoshi Hamamoto, Higashikagawa (JP); Takahiro Tanimoto, Higashikagawa (JP)

(73) Assignee: MEDRx Co., LTD, Higashikagawa-shi, Kagawa (JP)

( * ) Notice: Subject to any disclaimer, the term of this patent is extended or adjusted under 35 U.S.C. 154(b) by 0 days.

(21) Appl. No.: 15/279,272

(22) Filed: Sep. 28, 2016

(65) Prior Publication Data

US 2017/0056503 A1    Mar. 2, 2017

Related U.S. Application Data

(63) Continuation of application No. PCT/JP2016/075204, filed on Aug. 29, 2016, and a continuation-in-part of application No. PCT/JP2015/074552, filed on Aug. 29, 2015.

(51) Int. Cl.
| | |
|---|---|
| A61K 9/70 | (2006.01) |
| A61K 47/12 | (2006.01) |
| A61K 47/02 | (2006.01) |
| A61K 31/485 | (2006.01) |
| A61K 47/18 | (2017.01) |
| A61K 31/433 | (2006.01) |
| A61K 47/14 | (2017.01) |

(52) U.S. Cl.
CPC ............ *A61K 47/12* (2013.01); *A61K 9/7038* (2013.01); *A61K 9/7053* (2013.01); *A61K 31/433* (2013.01); *A61K 31/485* (2013.01); *A61K 47/02* (2013.01); *A61K 47/14* (2013.01); *A61K 47/18* (2013.01)

(58) Field of Classification Search
CPC .................................................... A61K 9/7038
See application file for complete search history.

(56) References Cited

U.S. PATENT DOCUMENTS

| | | | |
|---|---|---|---|
| 4,626,539 A * | 12/1986 | Aungst ............... | A61K 9/0014 514/282 |
| 8,623,387 B2 | 1/2014 | Yamaguchi et al. | |
| 2011/0028880 A1 | 2/2011 | Uchida et al. | |
| 2014/0066471 A1* | 3/2014 | Yamaguchi .......... | A61K 9/0014 514/282 |
| 2014/0170205 A1 | 6/2014 | Uchida et al. | |
| 2015/0174249 A1 | 6/2015 | Hamamoto et al. | |

FOREIGN PATENT DOCUMENTS

| | | |
|---|---|---|
| WO | WO 2009/066457 | 5/2009 |
| WO | WO 2009/107479 | 9/2009 |
| WO | WO 2010/073326 | 7/2010 |
| WO | WO 2010/098230 | 9/2010 |
| WO | WO 2012/165254 | 12/2012 |
| WO | WO 2013/191187 | 12/2013 |

\* cited by examiner

*Primary Examiner* — Benjamin Packard
(74) *Attorney, Agent, or Firm* — Knobbe, Martens, Olson & Bear, LLP

(57) ABSTRACT

An object of the present invention is to provide a patch preparation having an excellent skin permeability of medicament using an acid additional salt of basic medicament. Provided is a patch preparation comprising a support and an adhesive layer on one surface of the support, wherein the adhesive layer contains a basic medicament, a fatty acid-based ionic liquid, and potassium salts and/or potassium ions. Said potassium salts and/or potassium ions are generated as a result of reaction of an acid addition salt of the basic medicament with a compound capable of generating potassium ion in the adhesive layer.

14 Claims, No Drawings

PATCH PREPARATION CONTAINING AN ACID SCAVENGER

INCORPORATION BY REFERENCE TO ANY PRIORITY APPLICATIONS

Any and all applications for which a foreign or domestic priority claim is identified in the Application Data Sheet as filed with the present application are hereby incorporated by reference under 37 CFR 1.57.

BACKGROUND OF THE INVENTION

Technical Field

The present invention relates to a patch preparation containing an acid addition salt of a basic medicament as active ingredient, more specifically, a patch preparation in which a scavenger of acid attached to the medicament is contained to encourage production of free base.

Description of the Related Art

An example of a known technique for accelerating the transdermal absorption of a medicament is dissolving the medicament in a fatty acid-based ionic liquid (Patent Document 1).

On the other hand, basic medicament is often distributed in its acid addition salt such as hydrochloride salt. However, acid addition salt like that has tendency exhibit lower transdermal permeability relative to its free base. Therefore, it has been proposed to eliminate acid addition salt in drug formulation by adding neutralizing agent such as sodium hydroxide (Patent Document 2). In the document, problems of agglomeration or growth of metal salt with time which are produced by the neutralize reaction are solved with use of absorbent. However, a satisfying result for transdermal permeability had not given.

PRIOR ART DOCUMENTS

Patent Documents

Patent Document 1: WO2009/066457
Patent Document 2: WO2009/107479

SUMMARY OF THE INVENTION

Problem to be Solved

The object of the present invention is to provide a patch preparation having an excellent transdermal permeability of medicament with use of acid addition salt of basic medicament as a raw material.

Means for Solving the Problem

The present inventors intensively investigated and found that above problems can be solved by adding a compound capable of generating a potassium ion to the adhesive layer containing acid addition salt of basic medicament and fatty acid-base ionic liquid. The acid which constitutes the acid addition salt is scavenged by potassium ion to generates a potassium salt.

More specifically, the present invention provides following (1) to (8).

(1) A patch preparation comprising a support and an adhesive layer on one surface of the support, wherein the adhesive layer contains a basic medicament, fatty acid-based ionic liquid, and potassium salt and/or potassium ions.

(2) The patch preparation according to above item (1), wherein said potassium salts and/or potassium ions are generated as a result of reaction of an acid addition salt of the basic medicament with a compound being capable of generating potassium ion in the adhesive layer.

(3) The patch preparation according to above item (1) or (2), wherein the basic medicament is an opioid pain reliever.

(4) The patch preparation according to any one of above items (1)-(3), wherein the fatty acid-based ionic liquid is selected from the group consisting of oleic acid-diisopropanolamine, levulinic acid-diisopropanolamine, sorbic acid-diisopropanolamine, and combination thereof.

(6) A composition for a patch preparation comprising a basic medicament; a fatty acid-based ionic liquid; and a potassium ion generating compound.

(7) A method for forming a patch comprising providing an acid addition salt of a basic medicament; providing a fatty acid and an organic amine compound for forming a fatty acid based ionic liquid; providing a compound capable of generating potassium ion; and forming an adhesive composition by mixing the acid addition salt of the basic medicament, the fatty acid, the organic amine compound, and the potassium ion generating compound in a polymer solution for forming an adhesive layer.

(8) The method according to above item (7), wherein the fatty acid and the organic amine compound are previously mixed to form the fatty-acid based ionic liquid, then obtained-fatty based ionic liquid is provided instead of the fatty acid and the organic amine compound.

Effects of the Invention

According the present invention, a patch preparation containing a basic medicament which exhibits excellent transdermal absorbability is provided.

DETAILED DESCRIPTION OF THE PREFERRED EMBODIMENT

The patch preparation of the present disclosure comprises an adhesive layer placed on one surface of a support which contains a basic medicament, fatty acid-based ionic liquid, and a potassium salt and/or a potassium ion.

Basic Medicament

As the basic medicament, any medicament which is generically distributed in its acid addition salt can be utilized. As the acid addition salt, inorganic acid salt such as hydrochloride salt, sulfate salt, and salt of hydrobromic acid; organic acid salt such as fumarate, maleate, citrate, and tartrate can be exemplified. In the present invention, the inorganic acid is preferable, hydrochloride salt is most preferable as the acid addition salt. When hydrochloride salt of basic medicament is used as active ingredient, the potassium salt included in the adhesive layer should be potassium chloride.

Example of the hydrochloride salt of basic medicament include opioid pain reliever such as morphine hydrochloride, oxycodone hydrochloride, hydromorphone hydrochloride, fentanyl hydrochloride, pethidine hydrochloride, and naloxone hydrochloride; topical anesthetic such as lidocaine hydrochloride, tetracaine hydrochloride, procaine hydrochloride; muscle relaxant suxametonium such as tizanidine hydrochloride, and eperisone hydrochloride; psychoneurotic agent such as imipramine hydrochloride, sertraline hydrochloride, fluoxetine hydrochloride, and paroxetine hydrochloride; simulant/antihypnotic agent such as methylphenidate hydrochloride, and methamphetamine hydrochloride;

antiparkinson agent such as ropinirole hydrochloride, and amantadine hydrochloride; antialzheimer agent such as donepezil hydrochloride can be exemplified. In the present disclosure, opioid pain reliever such as morphine hydrochloride, oxycodone hydrochloride, hydromorphone hydrochloride, fentanyl hydrochloride, and pethidine hydrochloride are preferred, and oxycodone hydrochloride and hydromorphone hydrochloride are most preferred in view of the high transdermal permeability in the disclosed patch preparation.

Compounds Capable of Generating Potassium Ion

The potassium salt included in the adhesive layer of the patch preparation of the present disclosure is produced in the adhesive layer during or after the manufacturing process, as a result of reaction of the acid addition salt of basic medicament with a compound capable of generating a potassium ion. Examples of compounds capable of generating a potassium ion include potassium hydroxide; potassium salt of organic acid such as potassium citrate, potassium acetate, potassium tartrate, potassium lactate, and potassium salt of $C_{4-20}$ fatty acid; potassium salt of inorganic salt such as potassium bicarbonate, potassium dihydrogen phosphate, dibasic potassium phosphate, and tripotassium phosphate. Examples of the potassium salt of $C_{4-20}$ fatty acid include potassium sorbate, potassium oleate, and potassium levulinate. In some embodiments, potassium hydroxide and potassium salt of fatty acid can be used alone or in combination.

In the past, a sodium compound such as sodium hydroxide has been considered as a preferred neutralizing agent for neutralizing acid addition salt of a basic medicament to generate its free base in drug formulations. The fatty acid-based ionic liquid is known not only as an excellent dissolution adjuvant but also as a percutaneous absorption accelerator for medicaments. There are cases where the medicament does not sufficiently dissolve in the solvent, when the acid additional salt of basic medicament and a sodium compound such as sodium hydroxide are tried to dissolve in a solvent. Even if they can be dissolved, a patch preparation which is prepared with the use of sodium compound has less skin permeability than a patch which is prepared with the use of potassium compound. An insufficient elimination of the acid addition salt is considered one of cause of the less skin permeability. In contrast, acid addition salt of basic medicament easily dissolves in a solvent containing fatty-acid based ionic liquid without residue, by the presence of a compound capable of generating potassium ion. A patch preparation which is prepared by the use of obtained solution has a far superior skin permeability to a patch prepared by the use of sodium compound.

The concentration of the compound capable of generating potassium ion can be within a range of about 0.6 mol to about 4.5 mol, about 0.8 to 2.0 mol, or about 0.8 mol to about 1.5 mol per 1 mol of the acid contained in the acid addition salt of basic medicament.

Fatty Acid-Based Ionic Liquid

A fatty acid-based ionic liquid is a salt of a fatty acid and an organic amine compound. The fatty acid-based ionic liquid can be formed in adhesive composition by adding fatty acid and organic amine compound to the adhesive composition, though it can also be prepared prior to adding it to the adhesive composition. The fatty acid includes $C_{5-20}$ saturated or unsaturated fatty acid. Specific examples include capric acid, sorbic acid, levulinic acid, lauric acid, myristic acid, palmitic acid stearic acid, isostearic acid, oleic acid can be exemplified. As the organic amine compound, $C_{4-9}$ alkanolamine can be utilized. Specifically, monoethanolamine, monoisopropanolamine, diethanolamine, diisopropanolamine, triethanolamine, triisopropanolamine, and trishydroxylmethylaminomethane can be utilized.

Examples of fatty acid-based ionic liquid include ionic liquid containing diisopropanolamine, such as equimolar salt of levulinic acid and diisopropanolamine, equimolar salt of capric acid and diisopropanolamine, equimolar salt of isostearic acid and diisopropanolamine, equimolar salt of oleic acid and diisopropanolamine, equimolar salt of sorbic acid and diisopropanolamine; fatty acid-based ionic liquid such as equimolar salt of triethanolamine and levulinic acid, equimolar salt of caproic acid and triethanolamine, equimolar salt of isostearic acid and triethanolamine, equimolar salt of oleic acid and triethanolamine, equimolar salt of sorbic acid and triethanolamine; fatty acid-based ionic liquid containing diethanolamine such as equimolar of levulinic acid diethanolamine, equimolar salt of capric acid and diethanolamine, equimolar salt of isostearic acid and diethanolamine, equimolar salt of oleic acid and diethanolamine, and equimolar salt of sorbic acid and diethanolamine. The formulation or the patch preparation may contain one or more fatty acid-based ionic liquid.

The concentration of the fatty acid-based ionic liquid can be selected from a range of about 0.2 to about 12 mol, about 0.4 mol to about 5 mol, about 0.5 to about 1.5 mol per 1 mol of basic medicament.

When opioid pain reliever is used as basic medicament, ionic liquid of diisopropanolamine can be used as the fatty acid-based ionic liquid in view of the improvement of transdermal absorbability. In some embodiments, levulinic acid-diisopropanolamine is used in combination with oleic acid-diisopropanolamine.

Adhesive Layer

Adhesive layer is composed of an appropriate adhesive polymer. As the adhesive polymer, acrylic polymer, rubber polymer, silicone based polymer, and vinyl ether polymer can be exemplified. In the present disclosure, rubber polymer such as styrene-isoprene-styrene block copolymer, styrene-butadiene-styrene block copolymer, polyisoprene, polyisobutylene, and polybutadiene can be used. When rubber polymer is used, the concentration may be from about 5% to about 40% by weight, or about 10% to about 30% by weight relative to the total weight of the adhesive layer.

When adhesive layer is composed of rubber polymer, it is preferred that the adhesive layer further contains tackifier resin, and softener. As the tackifier resin, rosin ester, hydrogenated rosin ester, rosin maleate, alicyclic saturated hydrocarbon resin, terpene resin, and polyolefin resin can be exemplified. The concentration of the tackifier resin can be from about 10% to about 35% by weight, about 20% to about 30% by weight, or about 22% to about 28% by weight relative to total weight of the adhesive layer. Examples of the softener include naphthenic process oil; vegetable oil such as camellia oil, castor oil; liquid rubber such as liquid polybutene and liquid isoprene; and liquid paraffin.

Other Transdermal Absorptive Accelerator

In some embodiments, the adhesive layer may further contains one or more organic solvents. In some embodiments, the organic solvent has percutaneous absorption accelerating effect, and examples include fatty acid, alcohols, and esters. As for the fatty acid, similar fatty acid to that constitutes above mentioned fatty acid-based ionic liquid can be used. Amount of the fatty acid can be form about 0.4 mol to about 5 mol, about 0.5 mol to about 3 mol, or about 0.8 mol to about 1.5 mol per 1 mol of fatty acid-based ionic liquid. Also, concentration of the fatty acid can be from about 0.5 to about 10%, or about 6% by weight relative to total weight of the adhesive layer.

As for the alcohols, mono valent alcohol such as capryl alcohol, lauryl alcohol, myristyl alcohol, cetyl alcohol, stearyl alcohol, and oleyl alcohol; divalent alcohol such as propylene glycol, butylene glycol, polyethylene glycol; trivalent alcohol such as glycerin can be exemplified. Additive amount of the alcohols can be from about 5% to about 30% by weight, about 8% to about 25% by weight, or about 10% to about 15% by weight relative to the total weight of the adhesive layer. In the present disclosure, oleyl alcohol can be used because it exhibits excellent transdermal permeability. Additive amount of oleyl alcohol can be from about 3% to about 15% by weight or about 8% to about 12% by weight relative to total weight of the adhesive layer. Oleyl alcohol can also be used in combination with the other alcohols.

As for the esters, carbonic ester such as propylene carbonate; fatty acid ester such as diethyl sebacate, isopropyl myristate, diisopyl adipate, myristyl permeate, stearyl stearate, medium chain fatty acid triglyceride can be exemplified.

In some embodiments, the adhesive layer further contains a filler. When filler is used, not only adhesive property but also drug release can be improved. The amount of filler can be from about 0.5% to about 5% by weight relative to total amount of the adhesive layer. As for the filler, hydrous silica, fumed silica, talc, crystalline cellulose, starch, carmellose, metal salt of carmellose can be exemplified. In some embodiments, fumed silica is used as the filling. In some embodiments, commercially available fumed silica, AEROSIL®, can be used.

The adhesive layer may further contain appropriate additives that are usually used for the adhesive layer of a patch preparation, for example, softener and antioxidant.

Some embodiments provide a preparation method of the patch preparation of the present disclosure. A fatty acid and an organic amine for forming a fatty acid-based ionic liquid are mixed together to yield a homogeneous solution. In some embodiments, an organic solvent may also be added if needed. The organic solvent may have a percutaneous absorption accelerating effect. Into the solution, an acid addition salt of a basic medicament and a compound capable of generating potassium ions are added and dissolved to form a composition for the patch preparation. In some embodiments, the solution may be heated (e.g. about 45-60° C.) if needed. In some embodiments, the fatty acid, the organic amine, the acid additional salt of the basic solution, and the compound capable of generating potassium ions are mixed together at the same time.

In this medicament composition, the acid attached to the basic medicament is eliminate and the free base of the basic medicament is therefore generated. On the other hand, potassium salts are generated from the reaction of the eliminated acid with the potassium ions.

Although these reactions may be completed during preparation of the composition, parts of the reactions can occur during the step of mixing with the material that forms the adhesive, during the step of coating onto the support, or during the step of drying. Additionally, the reaction may continue in the adhesive layer after production process is completed. A patch preparation in which both acid addition salt of basic medicament and potassium salt exist together in the adhesive layer is also within the scope of the present invention.

Once the medicament composition is formed, it is mixed with the material that forms the adhesive layer. In some embodiments, the adhesive layer may comprise a rubber polymer. For example, a rubber polymer and a tackifier resin are mixed with toluene and heated (about 60° C.) to yield a molten solution. The molten solution is mixed with previously prepared composition and filler to form an adhesive composition. Then it is coated on a surface of support (e.g., woven fabric, unwoven fabric, or PET film), then heated (about 80° C.) and dried to remove toluene, thereby forming an adhesive layer on the support.

EXAMPLES

Herein after the present disclosure is described in detail with examples. The present disclosure is not limited in any way by these examples.

Patch Preparation Containing Oxycodone

Patch preparations with the composition (weight %) shown in Table 1 were prepared. Transdermal permeability of the prepared patches was evaluated by Franz cell diffusion experiment. Pig skin was used for the experiment. Cumulative skin permeation amount at each sampling point are shown in Table 1.

TABLE 1

|  |  | Ex. 1-a M286 | Ex. 1-b M308 | Ex. 1-3 M307 | Ex. 1-d M294 | Ex. 1-e | Com. 1 M313 |
|---|---|---|---|---|---|---|---|
| Oxyco.HCl 3H$_2$O |  | 3.461 | 3.461 | 3.461 | 3.461 | 3.461 | 3.461 |
| Potassium hydroxide |  | 0.55 |  |  |  | 0.55 | 0.55 |
| Potassium sorbate |  |  |  | 1.4 | 1.3 |  |  |
| Sodium hydroxide |  |  |  |  |  |  | 0.34 |
| Diisopropanolamine |  | 1.5 | 1.5 | 1.5 |  | 0.7 | 1.5 |
| Triethanolamine |  |  |  |  | 2.2 |  |  |
| Levulinic acid |  | 1.0 |  | 0.8 | 1.0 | 1.0 | 1.0 |
| Oleic acid |  | 4.0 | 4.0 | 3.0 | 4.0 | 4.0 | 4.0 |
| Oleyl alcohol |  | 10.0 | 10.0 | 10.0 | 8.0 | 10.0 | 10.0 |
| Glycerin |  | 3.0 | 4.0 | 4.0 | 2.5 |  | 3.0 |
| Concentrated glycerin |  |  |  |  |  | 3.0 |  |
| Propylene carbonate |  | 4.0 | 5.0 | 5.0 | 2.5 | 5.0 | 5.0 |
| Medium-chain triglyceride |  | 10.0 | 10.0 | 10.0 | 10.0 | 10.0 | 10.0 |
| Liquid paraffin |  | 17.34 | 16.49 | 16.81 | 17.64 | 3.0 | 17.55 |
| AEROSIL ® |  | 3.0 | 3.0 | 3.0 | 3.0 | 3.0 | 3.0 |
| PX-1150N |  | 27.0 | 26.0 | 26.0 | 27.0 | 26.0 | 26.0 |
| SIS-5002 |  | 15.0 | 15.0 | 15.0 | 15.0 | 14.0 | 15.0 |
| Sodium pyrosulfite |  | 0.1 | 0.1 | 0.1 | 0.1 | 0.1 | 0.1 |
| Propyl gallate |  | 0.05 | 0.05 | 0.05 | 0.05 | 0.05 | 0.05 |
| Total |  | 100 | 100 | 100 | 97.00 | 100 | 100 |
| Cumulative skin permeation amount (μg/cm$^2$) | 2 hr | 1.72 |  |  |  | 0.5 | 0.3 |
|  | 4 hr | 12.5 | 2.2551 | 3.9967 | 1.86 | 5 | 1.8 |
|  | 6 hr | 40.32 | 7.0518 | 15.8 | 6.015 | 14.8 | 4 |
|  | 8 hr | 76.469 | 46.639 | 33.5 | 11.982 | 31.1 | 7.3 |
|  | 24 hr | 245.88 | 164.53 | 224.45 | 90.235 | 248.3 | 52.5 |
| (acid)/(base) |  | 1.08 | 1.14 | 1.32 | 0.93 | 1.51 | 1.15 |

All patches of Examples 1-a to 1-d, which contain compound capable of generating potassium ion as raw material, exhibit excellent skin permeability. Patch preparation of comparative Example 1 which containing sodium hydroxide instead of potassium hydroxide had poor skin permeability. Patch preparation of Example 1-d had less skin permeability than that of Examples 1-a to 1-c. It is considered because the patch of Example 1-d doesn't include fatty acid-based ionic liquid containing diisopropanolamine. Patch preparation of Example 1-a and 1-c had especially excellent skin permeability. It is considered because they contain both levulinic acid-diisopropanolamine and oleic acid-diisopropanolamine.

Patch Preparation Containing Hydromorphone

Patch preparations as the composition (weight %) shown in Table 2 were prepared. Transdermal permeability of the prepared patches was evaluated by Franz cell diffusion experiment. Pig skin was used for the experiment. Cumulative skin permeation amount at each sampling point are shown in Table 2.

|  |  | Ex. 2-a N511 | Ex. 2-b N488 | Com. 2-a S805 | Ex. 2-c S842 | Ex. 2-d S847 | Ex. 2-e S846 | Ex. 2-f S827 | Com. 2-b S826 |
|---|---|---|---|---|---|---|---|---|---|
| Hydromorphone hydrochloride | | 1.0 | .0 | 1.0 | 3.0 | 3.0 | 3.0 | 3.0 | 3.0 |
| Potassium hydroxide | | | | | | 1 | 0.4 | 0.61 | |
| Potassium sorbate | | 0.5 | 0.2 | | 1.4 | | 1.4 | | |
| Diisopropanolamine | | 1.5 | 1.5 | 1.5 | 1.5 | 1.5 | 1.5 | 1.5 | 1.5 |
| Triethanolamine | | 4.0 | 4.7 | 1.5 | | | | 1.5 | 1.4 |
| Levulinic acid | | | | | | 1.1 | | 1.1 | 1.1 |
| Oleic acid | | 6.0 | 6.0 | 6.0 | 3.0 | 3.0 | 3.0 | 6.0 | 3.0 |
| Sorbic acid | | 2.7 | 0.2 | | | | | | |
| Lactic acid | | | 2.0 | | | | | | |
| Sodium lactate | | | 1.6 | | | | | | |
| Oleyl alcohol | | | | 5.0 | 10.0 | 10.0 | 10.0 | 8.0 | 8.0 |
| Propylene glycol | | 5 | | | | | | | |
| PEG200 | | | 2.0 | | | | | | |
| Glycerin | | 7.0 | 7.0 | 5.0 | 4.0 | 4.0 | 4.0 | 3.0 | 4.0 |
| Propylene carbonate | | 5.0 | 5.0 | 5.0 | 5.0 | 5.0 | 5.0 | 2.5 | 5.0 |
| Medium-chain triglyceride | | | | | 10.0 | 10.0 | 10.0 | 10.0 | 10.0 |
| Diethyl sebacate | | 5.0 | 5.0 | 5.0 | | | | | |
| Isopropyl myristate | | 5.0 | 5.0 | 5.0 | | | | | |
| Liquid paraffin | | 12.15 | 14.65 | 18.85 | 17.95 | 17.27 | 17.55 | 17.64 | 17.85 |
| AEROSIL ® | | 4.0 | 3.0 | 3.0 | 3.0 | 3.0 | 3.0 | 3.0 | 3.0 |
| PX-1150N | | 27.0 | 27.0 | 28.0 | 26.0 | 26.0 | 26.0 | 27.0 | 27.0 |
| SIS-5002 | | 14.0 | 14.0 | 15.0 | 15.0 | 15.0 | 15.0 | 15.0 | 15.0 |
| Sodium pyrosulfite | | 0.1 | 0.1 | 0.1 | 0.1 | 0.1 | 0.1 | 0.1 | 0.1 |
| Propyl gallate | | 0.05 | 0.05 | 0.05 | 0.05 | 0.05 | 0.05 | 0.05 | 0.05 |
| Total | | 100.0 | 100.0 | 100.0 | 100.0 | 100.0 | 100.0 | 100.0 | 100.0 |
| Cumulative | 2 hr | | | | 0.3198 | | | 0.9786 | |
| skin | 4 hr | 0.472 | 0.348 | 0.965 | 0.5907 | | 0.6 | 5.759 | 0.458 |
| permeation | 8 hr | 2.941 | 3.095 | 6.107 | 10.274 | 3.9 | 7.5 | 25.721 | 7.3018 |
| amount ($\mu g/cm^2$) | 24 hr | 36.21 | 27.88 | 15.33 | 68.594 | 71.9 | 87.8 | 75.724 | 38.435 |
| (acid)/(base) | | 1.36 | 0.79 | 1.11 | 0.97 | 0.69 | 0.72 | 1.02 | 1.08 |

Patch preparation of Examples 2-a and 2-b containing potassium sorbate exhibited superior skin permeability to that Comparative Example 2-a which does not contain any compound capable of generating potassium ion. Patch preparations of Examples 2-c and 2-f containing compound capable of generating potassium ion exhibited superior skin permeability to that of Comparative Example 2-b which doesn't contain such compound.

Patch Preparation Containing Tizanidine Hydrochloride

Patch preparations as the composition (weight %) shown in Table 3 were prepared. Transdermal permeability of the prepared patches was evaluated by Franz cell diffusion experiment. Pig skin was used for the experiment. Cumulative skin permeation amount at each sampling point are shown in Table 3.

TABLE 3

|  | Ex. 3-a T651 | Ex. 3-b T695 | Ex. 3-c T697 | Ex. 3-d T700 | Ex. 3-e T702 | Ex. 3-f T696 |
|---|---|---|---|---|---|---|
| Tizanidine hydrochloride | 1.72 | 1.72 | 1.72 | 1.72 | 1.72 | 1.72 |
| Sorbic acid | 0.66 | | | | | |
| Potassium sorbate | 0.89 | 0.89 | 0.89 | 0.89 | 0.89 | 0.89 |
| Oleic acid | | 1.50 | 1.50 | 1.50 | 1.50 | 1.50 |
| Triethanolamine | 0.5 | 0.5 | 0.4 | | | |
| Oleyl alcohol | 10.0 | 10.0 | 10.0 | 10.0 | 10.0 | 10.0 |
| Myristyl alcohol | | 3.0 | 3.0 | | 3.0 | 3.0 |
| Glycerin | 5.0 | 5.0 | 5.0 | 5.0 | 5.0 | 5.0 |
| DiPG | 4.0 | 4.0 | 4.0 | 4.0 | 4.0 | 4.0 |

TABLE 3-continued

|  | Ex. 3-a T651 | Ex. 3-b T695 | Ex. 3-c T697 | Ex. 3-d T700 | Ex. 3-e T702 | Ex. 3-f T696 |
|---|---|---|---|---|---|---|
| BG | 3.0 | 3.0 | 3.0 | 3.0 | 3.0 | 3.0 |
| Medium-chain triglyceride | 5.0 | | | | | |
| AEROSIL ® | 3.0 | 3.0 | | 3.0 | 3.0 | 3.0 |
| Liquid paraffin | 18.08 | 23.24 | 23.34 | 26.74 | 23.74 | 23.74 |
| Terpene resin | 32.00 | 28.00 | 28.00 | 28.00 | 28.00 | 28.00 |
| SIS-5002 | 16.00 | 16.00 | 16.00 | 16.00 | 16.00 | 16.00 |
| Sodium sulfite | | 0.10 | 0.10 | 0.10 | 0.10 | 0.10 |

TABLE 3-continued

|  |  | Ex. 3-a T651 | Ex. 3-b T695 | Ex. 3-c T697 | Ex. 3-d T700 | Ex. 3-e T702 | Ex. 3-f T696 |
|---|---|---|---|---|---|---|---|
| Sodium pyrosulfite | | 0.10 | | | | | |
| Propyl gallate | | 0.05 | 0.05 | 0.05 | 0.05 | 0.05 | 0.05 |
| Total | | 100 | 100 | 100 | 100 | 100 | 100 |
| Cumulative skin permeation amount ($\mu g/cm^2$) | 4 hr | 0.4 | 2.1 | 1.9 | 3.6 | 0.8 | 2.4 |
| | 6 hr | 1.6 | 5.8 | 5.7 | 7.0 | 2.7 | 8.5 |
| | 8 hr | 4.5 | 10.5 | 11.0 | 12.0 | 6.1 | 17.7 |
| | 22 hr | 84.0 | 51.2 | 54.5 | 68.7 | 57.8 | 105.2 |
| | 24 hr | 98.5 | 56.1 | 58.9 | 77.3 | 66.4 | 112.5 |

All patches of Examples 3-a to 3-f containing potassium sorbate which is capable of generating potassium ion exhibited excellent skin permeability.

INDUSTRIAL APPLICABILITY

The patch preparation of the present invention exhibit excellent skin permeability. Especially has high use value as patch preparation containing opioid pain reliever such as oxycodone hydrochloride and hydromorphone hydrochloride.

What is claimed is:

1. A patch preparation comprising:
   a support;
   an adhesive layer on one surface of the support;
   wherein the adhesive layer comprises oxycodone, a fatty acid-based ionic liquid, and potassium salts and/or potassium ions; and
   a molar ratio of the fatty acid-based ionic liquid to the oxycodone is between about 0.4 to about 5.

2. The patch preparation according to claim 1,
   wherein said potassium salts and/or potassium ions are generated as a result of reaction of an acid addition salt of the oxycodone with a compound capable of generating potassium ion in the adhesive layer.

3. The patch preparation according to claim 2, wherein the acid addition salt is selected from the group consisting of hydrochloride salt, sulfate salt, and salt of hydrobromic acid.

4. The patch preparation according to claim 1, wherein the potassium salt is potassium hydrochloride.

5. The patch preparation according to claim 1, wherein the fatty acid-based ionic liquid is selected from the group consisting of oleic acid-diisopropanolamine, levulinic acid-diisopropanolamine, sorbic acid-diisopropanolamine, and a combination thereof.

6. A composition for a patch preparation comprising:
   An acid addition salt of a oxycodone;
   a fatty acid-based ionic liquid;
   a potassium ion generating compound; and
   wherein a molar ratio of the fatty acid-based ionic liquid to the oxycodone is between about 0.4 to about 5.

7. The composition of claim 6, wherein the fatty acid-based ionic liquid is selected from the group consisting of oleic acid-diisopropanolamine, levulinic acid-diisopropanolamine, sorbic acid-diisopropanolamine, and a combination thereof.

8. The composition of claim 6, wherein the potassium ion generating compound is selected from the group consisting of potassium hydroxide, potassium citrate, potassium acetate, potassium tartrate, potassium lactate, potassium bicarbonate, potassium dihydrogen phosphate, dibasic potassium phosphate, tripotassium phosphate, potassium sorbate, potassium oleate, potassium levulinate, and a combination thereof.

9. A method for forming a patch, comprising:
   providing an acid addition salt of a oxycodone;
   providing a fatty acid and an organic amine compound for forming a fatty acid-based ionic liquid;
   providing a potassium ion generating compound;
   forming an adhesive composition by mixing the acid addition salt of oxycodone, the fatty acid, the organic amine, and the potassium ion generating compound in a polymer solution for forming an adhesive layer, wherein a molar ratio of the fatty acid-based ionic liquid to the oxycodone is between about 0.4 to about 5.

10. The method of claim 9, wherein the fatty acid and the organic amine compound are mixed to form the fatty acid-based ionic liquid prior to mixing with the acid addition salt of oxycodone and the potassium ion generating compound.

11. The method of claim 9, further comprising forming a potassium salt and the oxycodone in the adhesive composition by reacting the potassium generating compound with the acid addition salt of oxycodone.

12. The method of claim 9, wherein the fatty acid is a $C_{5-20}$ saturated or unsaturated fatty acid.

13. The method of claim 9, wherein the organic amine compound is a $C_{4-9}$ alkanolamine.

14. The method of claim 9, wherein the potassium ion generating compound is selected from the group consisting of potassium hydroxide, potassium citrate, potassium acetate, potassium tartrate, potassium lactate, potassium bicarbonate, potassium dihydrogen phosphate, dibasic potassium phosphate, tripotassium phosphate, potassium sorbate, potassium oleate, potassium levulinate, and a combination thereof.

* * * * *